United States Patent
Wurm et al.

(10) Patent No.: US 8,357,823 B2
(45) Date of Patent: *Jan. 22, 2013

(54) ALKYLENE OXIDE CAPPED SECONDARY ALCOHOL ETHOXYLATES AS FERMENTATION FOAM CONTROL AGENTS

(75) Inventors: David Bradley Wurm, Pearland, TX (US); Yuri Alencar Marques, Botucatu (BR)

(73) Assignees: Dow Global Technologies LLC; Dow Brasil Sudeste Industrial LTDA (BR)

( * ) Notice: Subject to any disclaimer, the term of this patent is extended or adjusted under 35 U.S.C. 154(b) by 513 days.

This patent is subject to a terminal disclaimer.

(21) Appl. No.: 12/561,466

(22) Filed: Sep. 17, 2009

(65) Prior Publication Data

US 2010/0075389 A1    Mar. 25, 2010

Related U.S. Application Data

(60) Provisional application No. 61/099,661, filed on Sep. 24, 2008.

(51) Int. Cl.
*C07C 43/13* (2006.01)
(52) U.S. Cl. ........................................ 568/622; 568/679
(58) Field of Classification Search .................. None
See application file for complete search history.

(56) References Cited

U.S. PATENT DOCUMENTS

| | | | |
|---|---|---|---|
| 3,359,331 A | 12/1967 | Baker et al. | |
| 3,539,519 A | 11/1970 | Weimer | |
| 4,152,592 A | 5/1979 | Molina | |
| 4,340,766 A | 7/1982 | Klahr et al. | |
| 4,753,885 A | 6/1988 | Dietsche et al. | |
| 4,836,951 A | 6/1989 | Totten et al. | |
| 4,898,621 A | 2/1990 | Pruehs et al. | |
| 4,927,954 A | 5/1990 | Knopf et al. | |
| 4,942,049 A | 7/1990 | Schmid et al. | |
| 5,525,702 A | 6/1996 | Nace | |
| 5,576,281 A | 11/1996 | Bunch et al. | |
| 5,766,371 A | 6/1998 | Bunch et al. | |
| 5,912,209 A | 6/1999 | Kassebaum et al. | |
| 6,057,375 A | 5/2000 | Wollenweber et al. | |
| 6,083,998 A * | 7/2000 | Romualdo et al. | 516/117 |
| 6,680,412 B2 | 1/2004 | Gumbel et al. | |
| 6,693,065 B2 | 2/2004 | Gentilhomme et al. | |
| 2005/0014979 A1 | 1/2005 | Eleveld et al. | |
| 2005/0170991 A1 | 8/2005 | Ruland et al. | |
| 2006/0069220 A1 | 3/2006 | Meurs et al. | |
| 2007/0275122 A1 | 11/2007 | Cazaroto et al. | |
| 2010/0267844 A1 | 10/2010 | Varineau et al. | |

FOREIGN PATENT DOCUMENTS

| | | |
|---|---|---|
| EP | 0389157 | 9/1990 |
| EP | 0850907 B1 | 9/2004 |
| EP | 1454667 | 9/2004 |
| GB | 899222 | 6/1962 |
| JP | 10192685 | 7/1998 |
| WO | 9612001 | 4/1996 |
| WO | 0141909 | 6/2001 |
| WO | 2005039732 | 5/2005 |

OTHER PUBLICATIONS

Rakutani, et al. "Secondary alcohol ethoxylates," Annual Surfactants Review (1999) 2, 216-247.
International Search Report and Written Opinion for PCT/US2009/057250 dated May 7, 2010.
XP002522729, abstract for JP11323754, dated Nov. 1999.
XP002522671, abstract of JP3131698, published Jun. 1991.
J.H. Mcfarland, et al., Performance and Properties of Nonionic Surfactants from Linear Secondary Alcohols, 1964, Union Carbide Chemicals Division, Research and Development Department, vol. 41, pp. 742-746.
N. Kurata, et al., Secondary Alcohol Ethoxylates, American Chemical Society, 1981, pp. 113-157.

* cited by examiner

*Primary Examiner* — Rosalynd Keys

(57) ABSTRACT

Provided are foam control agents and their use for controlling foam in fermentation processes. The foam control agents are of the formula I:

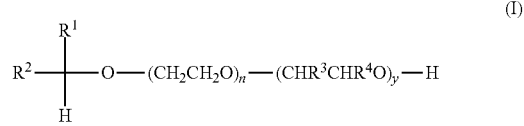

wherein $R^1$, $R^2$, $R^3$, $R^4$, n and y are as defined herein.

15 Claims, 2 Drawing Sheets

ALKYLENE OXIDE CAPPED SECONDARY ALCOHOL ETHOXYLATES AS FERMENTATION FOAM CONTROL AGENTS

This application claims priority to U.S. provisional Ser. No. 61/099,661, filed Sep. 24, 2008, which is incorporated herein by reference in its entirety.

FIELD OF THE INVENTION

The invention relates to compounds and methods for controlling foaming in fermentation processes.

BACKGROUND OF THE INVENTION

Foam formation during fermentation processes is a well know problem. Typically, the foam at the air-liquid interface is elastic in character and as such readily traps fermentation gases rising to the surface. As the foam is relatively resistant to being broken, the gases remain in the top part of the liquid causing additional bubbles and increasing the volume of the foam. Unless rigorously controlled, the foam can cause fermentation tank overflow, which can result in loss of broth, loss of organism, such as yeast, and/or loss of product (e.g., ethanol).

Foam control agents are well known and used in the fermentation industry. There is a need for new foam control materials that exhibit increased potency and/or are longer lasting than those currently being used.

BRIEF SUMMARY OF THE INVENTION

In one aspect, the invention provides foam control agents. The foam control agents are of the formula I:

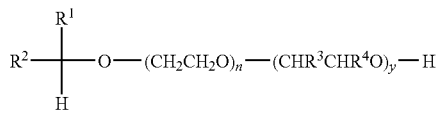

(I)

wherein $R^1$ and $R^2$ are each independently hydrogen or a linear or branched alkyl group containing from 1 to about 18 carbon atoms, provided that $R^1$ and $R^2$ together contain from about 8 to about 18 carbon atoms, and further provided that less than about 10 mole percent of $R^1$ or $R^2$ is hydrogen; $R^3$ and $R^4$ are each independently hydrogen or an alkyl radical containing from 2 to about 6 carbon atoms, provided that $R^3$ and $R^4$ together contain from 2 to about 6 carbon atoms; n is an average value ranging from about 3 to about 40; and y is an average value ranging from about 0.5 to about 5.

In another aspect, the invention provides methods for preventing or controlling foaming in fermentation processes. The method comprises using in the fermentation process a foam control agent of formula I.

DETAILED DESCRIPTION OF THE INVENTION

Figure 1:
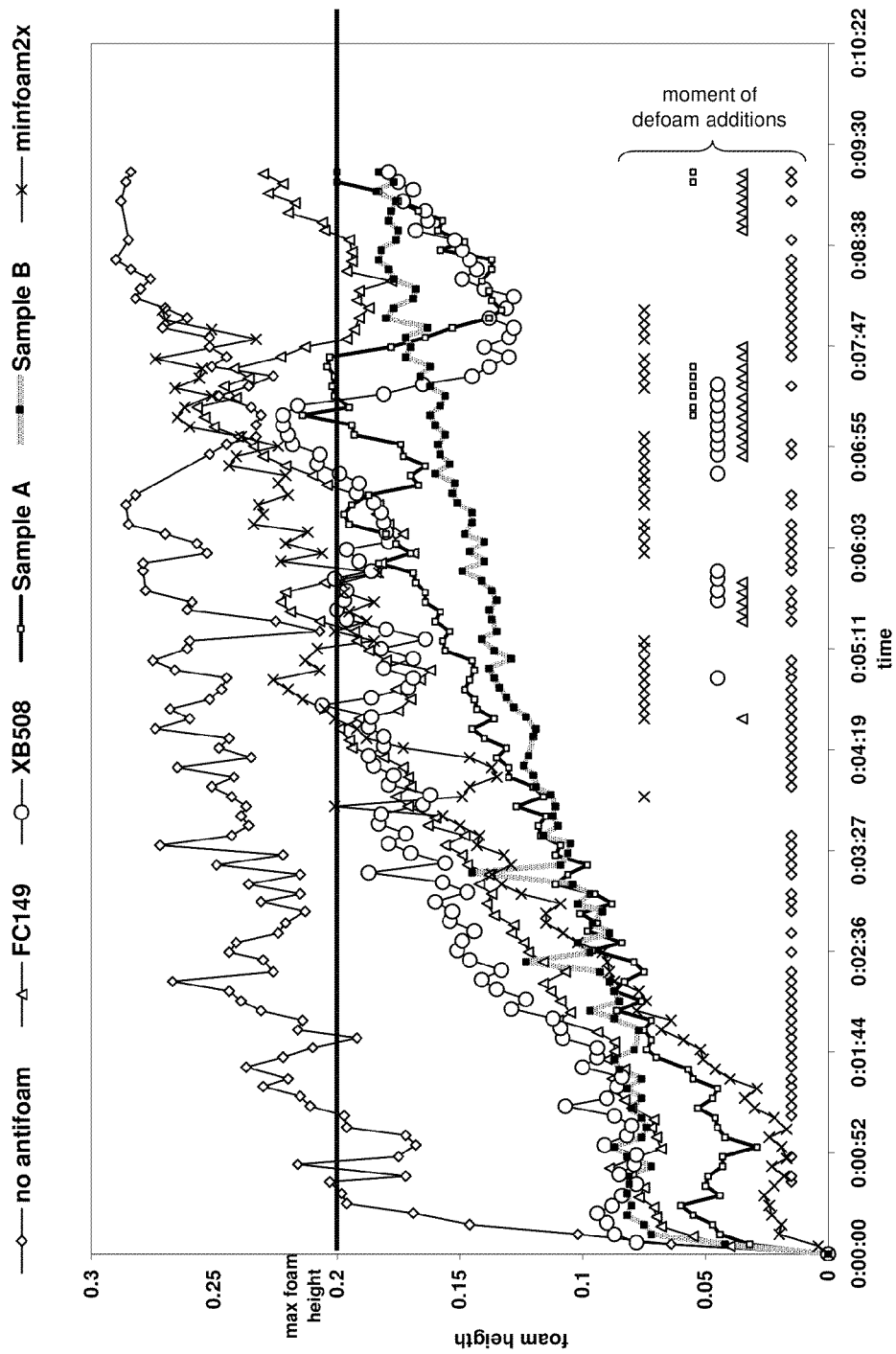
FIG. 1 is a plot of foam height as a function of time and number of additions for foam control agents according to the invention compared with commercial products.

As noted above, the invention provides foam control agents. The agents are particularly suitable for controlling foaming in fermentation processes, such as those used for manufacturing biofuels, for example, ethanol. The foam control agents of the invention are of the formula I:

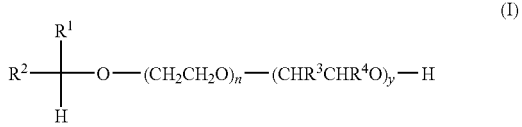

(I)

wherein $R^1$ and $R^2$ are each independently hydrogen or a linear or branched alkyl group containing from 1 to about 18 carbon atoms, provided that $R^1$ and $R^2$ together contain from about 8 to about 18 carbon atoms, and further provided that less than about 10 mole percent of $R^1$ or $R^2$ is hydrogen; $R^3$ and $R^4$ are each independently hydrogen or an alkyl radical containing from 2 to about 6 carbon atoms, provided that $R^3$ and $R^4$ together contain from 2 to about 6 carbon atoms; n is an average value ranging from about 3 to about 40; and y is an average value ranging from about 0.5 to about 5.

As demonstrated by the Examples below, the foam control agents of the invention are generally superior to agents currently used in the fermentation industry. For instance, the foam control agents of the invention can control foam formation for a longer time than currently known agents. The foam control agents of the invention are also generally biodegradable.

Preferred foam control agents of formula I are those in which $R^1$ and $R^2$ are each independently hydrogen or a linear or branched alkyl group containing from 1 to about 15 carbon atoms and $R^1$ and $R^2$ together contain from about 8 to about 16 carbon atoms. More preferably, $R^1$ and $R^2$ are each independently hydrogen or a linear or branched alkyl group containing from 1 to about 14 carbon atoms and $R^1$ and $R^2$ together contain from about 9 to about 14 carbon atoms.

Also preferred are agents in which y ranges from about 0.5 to about 3.5, more preferably from about 1 to about 2.5, and even more preferably from about 1.5 to about 2.5, and particularly preferably from about 1.6 to about 2.3

Further preferred are agents in which $R^3$ and $R^4$ together contain 2 carbon atoms.

Additionally preferred are compounds in which $R^3$ is H and $R^4$ is ethyl.

Particularly preferred foam control agents for use in the invention include those of formula II:

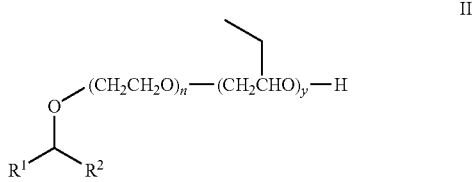

II wherein n is an average value ranging from about 3 to about 15, more preferably about 9 to about 12; and y is an average value ranging from about 0.5 to about 5, more preferably about 1 to about 2.5.

In a preferred embodiment, n in formula II is 9. In a further preferred embodiment, n is 12.

In a still further preferred embodiment, $R^1$ and $R^2$ are each independently hydrogen or a linear or branched alkyl group containing from 1 to about 14, more preferably each is a linear or branched alkyl containing 2-12 carbon atoms. Also preferably $R^1$ and $R^2$ together contain from about 11 to about 13 carbon atoms. Particularly preferably, $R^1$ and $R^2$ together with the carbon to which they are attached form linear dodecane. The oxide branch can be positioned at any location along the dodecane chain. Preferably, the oxide branch is on the 6th carbon. A particularly preferred foam control agent is of the formula:

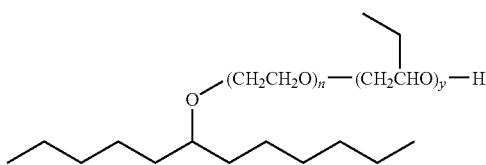

wherein n and y are as defined above.

As noted, the compounds of formula I are useful for controlling foaming in fermentation processes. Such processes include, for instance, the production of ethanol and other biofuels. The foam control agents of the invention may be used as antifoamers and/or defoamers in any desired amount so as to prevent, reduce, or eliminate the formation of foam. Those skilled in the art will be able to determine usage amounts via a combination of general knowledge of the applicable field as well as routine experimentation where needed. Typically, the agent is used at a concentration of from about 1 to about 1000 ppm, preferably from about 1 to about 100 ppm, and more preferably from about 3 to about 30 ppm, based on the total weight of the fermentation broth.

As will be understood by those skilled in the art, additional ingredients may be used with the materials of the invention to further enhance their effectiveness. For example, using other antifoaming and/or defoaming agents or surfactants with the agents of the invention may, in some circumstances, be desirable.

Fermentation processes are well known in the art and typically involve mixing a sugars solution, such as but not limited to sugarcane juice, and a fermenting microorganism, such as baker's yeast *Saccharomyces*, in a batch or continuous reactor, and fermenting the mixture to product formation.

Although there is no particular limitation on when in the fermentation process the foam control agent should be added, it is generally preferred to add the material during loading of the fermentation reactor with the sugar solution and the microorganism or directly to the yeast, or even in the fermentation reactor during the fermentation process.

The foam control agents of the invention may be prepared in a convenient and cost-effective manner. The starting materials include, first, at least one linear or branched secondary alcohol. This alcohol preferably contains a total of from about 7 to about 18 carbon atoms, more preferably from about 8 to about 16 carbon atoms. In particularly preferred embodiments, the alkyl group of the alcohol contains from about 11 to about 15 carbon atoms. Suitable alcohols include, for example, linear or branched isomers of the following: 2-decanol, 3-decanol, 4-decanol, 5-decanol, 2-undecanol, 3-undecanol, 4-undecanol, 5-undecanol, 2-dodecanol, 3-dodecanol, 4-dodecanol, 5-dodecanol, 6-dodecanol, 2-tridecanol, 3-tridecanol, 4-tridecanol, 5-tridecanol, 6-tridecanol, 2-tetradecanol, 3-tetradecanol, 4-tetradecanol, 5-tetradecanol, 6-tetradecanol, 7-tetradecanol, 2-pentadecanol, 3-pentadecanol, 4-pentadecanol, 5-pentadecanol, 6-pentadecanol, 7-penta-decanol, 2-hexadecanol, 3-hexadecanol, 4-hexadecanol, 5-hexadecanol, 6-hexadecanol, 7-hexadecanol, 8-hexadecanol, and combinations thereof. A particularly preferred alcohol is 6-dodecanol.

Up to about 10 mole percent of one or more primary alcohols having carbon chain lengths ranging from about C10 to about C16 may, in some embodiments, be included with the secondary alcohols specified above, but such inclusion is not required. Non-limiting examples of suitable primary alcohols include 1-decanol, 1-undecanol, 1-dodecanol, 1-tridecanol, 1-tetradecanol, 1-pentadecanol, and 1-hexadecanol.

Generally, the foam control agents are prepared by reacting the linear or branched secondary alcohol, or mixture of alcohols, with ethylene oxide. This reaction serves to increase the effective molecular weight of the hydrophilic portion of the molecule by the addition of ethylene oxide. For example, in some non-limiting embodiments the desired degree of ethoxylation, represented by the subscript n in Formula I, has values ranging from about 3 to about 40. In preferred embodiments, n ranges from about 3 to about 20. In even more preferred embodiments, n ranges from about 3 to about 12.

The methods and conditions used for this ethoxylation step may be any that are known to those skilled in the art. For example, in one non-limiting embodiment, this reaction may be carried out at an elevated temperature or temperatures ranging from about 20° C. to about 180° C. In other non-limiting embodiments, the temperature may range from about 100° C. to about 160° C. Pressures from about 14 psig to about 60 psig may, in certain non-limiting embodiments, be particularly efficacious, but other pressures may also be effectively employed. Those skilled in the art will be able to determine appropriate conditions with, at most, routine experimentation. Further discussion concerning preparation of secondary alcohol alkoxylates may be found in, for example, Rakutani, et al., "Secondary alcohol ethoxylates," *Annual Surfactants Review* (1999) 2, 216-247, which is incorporated herein by reference in its entirety.

In some non-limiting embodiments the ethoxylation (represented by the subscript n in Formula I) may be carried out in the presence of an effective amount of a suitable acidic catalyst, such as a boron trifluoride etherate solution, in order to increase the rate and/or yield of the reaction. Metal cyanide catalysts may alternatively be employed. The amount of the catalyst may, in such embodiments, range from about 0.005 percent to about 1 percent by weight, based on the alcohol. Sufficient ethylene oxide is added to provide a preferred product molecular weight range from about 300 to about 1400. Following the addition reaction, the product may be neutralized with a base, such as sodium hydroxide, and then purified via distillation to remove unreacted alcohol and residual catalyst.

In the second, the product of the ethoxylation is capped with a second alkoxylene oxide, using known alkoxylation techniques. The capped portion of the molecule represented by Formula I hereinabove is represented as the group containing the subscript y. For this final capping alkoxylation, exemplary alkylene oxides include butylene oxide, pentene oxide, hexene oxide, heptene oxide, or octene oxide, or any combination thereof. The amount of alkylene oxide used for the capping may range from about 0.5 to about 5 times stoichiometric, and in certain particular embodiments, it may range from about 0.5 to about 3.5, or from about 1 to about 3, times stoichiometric. While a variety of alkylene oxides is suitable for use in this second step alkoxylation, in certain non-limiting embodiments butylene oxide may be particularly efficacious. One advantage of using butylene oxide, rather than, for example, a lower alkylene oxide such as propylene oxide for this capping is that a reduced molar amount of butylene oxide serves to comparably suppress foam and reduce the cloud point of the composition. Therefore, the end product may be less expensive to produce than surfactants based on lower alkylene oxide capping.

Use of a linear or branched secondary alcohol as a starting material for the formation of the foaming agents of the invention may result in a final, capped product offering improved handling, higher solubility and narrower gel range in water, better wetting power, and reduced foaming (forming more unstable foams), when compared with, for example, alkoxylated nonionic surfactants based on linear primary alcohols.

The methods used for the alkylene oxide capping may be any that are known to those skilled in the art. For example, in one embodiment, this reaction may be carried out at an elevated temperature or temperatures in a range from about 20° C. to about 180° C. In certain particular embodiments, the temperature may range from about 60° C. to about 160° C. Pressures from about 14 psig to about 60 psig may, in certain non-limiting embodiments, be employed, but other pressures may also be suitably efficacious. Those skilled in the art will be able to determine appropriate and/or optimized conditions and methodology upon, at most, routine experimentation.

In some non-limiting embodiments the capping alkoxylation may be carried out in the presence of an effective amount of a suitable alkaline catalyst, such as a hydroxide of an alkali metal or alkaline earth metal. A particularly convenient catalyst, in some non-limiting embodiments, is potassium hydroxide. The amount of alkaline catalyst may, in such embodiments, range from about 0.005 percent to about 1 percent by weight, based on the alcohol. Following the reaction, the product may be neutralized with an acid, such as phosphoric acid or acetic acid. Acetic acid is advantageous because the soluble acetate salts may, in some embodiments, be left in the product so no filtration step would be necessary. The product may be used as is, or further purified, such as by distillation.

The foam control agents of formula I, prepared as described above, are generally block copolymers that are based on secondary alcohols.

The following examples are illustrative of the invention but are not intended to limit its scope.

EXAMPLES

Example 1

Comparison of Foam Control Agents of the Invention to Commercially Available Products This example compares foam control agents of the invention with commercially available products for foam control in bioethanol production.

The materials of the invention are as follows:

Invention Sample A: formula II material in which n is 9, y is about 1.5, and $R^1$ and $R^2$ and the carbon to which they are attached from a linear dodecane chain. The oxide branch is on the 6th carbon.

Invention Sample B: formula II material in which n is 12 and y is about 1.5, and $R^1$ and $R^2$ and the carbon to which they are attached from a linear dodecane chain. The oxide branch is on the 6th carbon.

The commercially available products (which are not examples of the invention) are as follows:

FLUENT-CANE™ 149 Polyglycol (FC149): An EO/PO block copolymer polyol available from The Dow Chemical Company.

TERGITOL™ Minfoam 2X: a random copolymer based on ethylene oxide and propylene oxide available from The Dow Chemical Company.

XB81508.00 Polyglycol (XB508), a commercial EO/PO block copolymer polyol (having a different block structure than FC149) available from The Dow Chemical Company.

In this example, an experimental apparatus is used to generated and measure foam height during bioethanol production. Prior to testing (no considerable bioethanol is produced in the test), a foam control agent is added to the fermentation broth to minimize foam formation during the fermentation process. Once the foam reaches a certain height, a defoamer such as mineral oil is added to again reduce the foam below a certain level. Each time the foam height reaches a certain level, more defoamer is added to again reduce the foam to the desired height. Measuring foam height and the required number of additions of defoamer in this way permits one to gauge the efficacy of a foam control agent. The results of such an experiment involving the compounds of the present invention are shown in FIG. 1. The results of this experiment are also summarized in Table 1.

TABLE 1

| Product | Adds of defoam |
| --- | --- |
| NO ANTIFOAM (comparative example) | 179 |
| FC149 300 ul (comparative example) | 38 |
| XB508 300 ul (comparative example) | 21 |
| Invention Sample A 300 ul (invention example) | 12 |
| Invention Sample B 300 ul (invention example) | 0 |
| Minfoam 2x 300 ul (comparative example) | 72 |

For each example, 300 microliters of foam control agent is added to the fermentation tank. "Adds of defoam" refers to the number of additions of defoamer, such as mineral oil, that is required to reduce the foam level.

Figure 2:
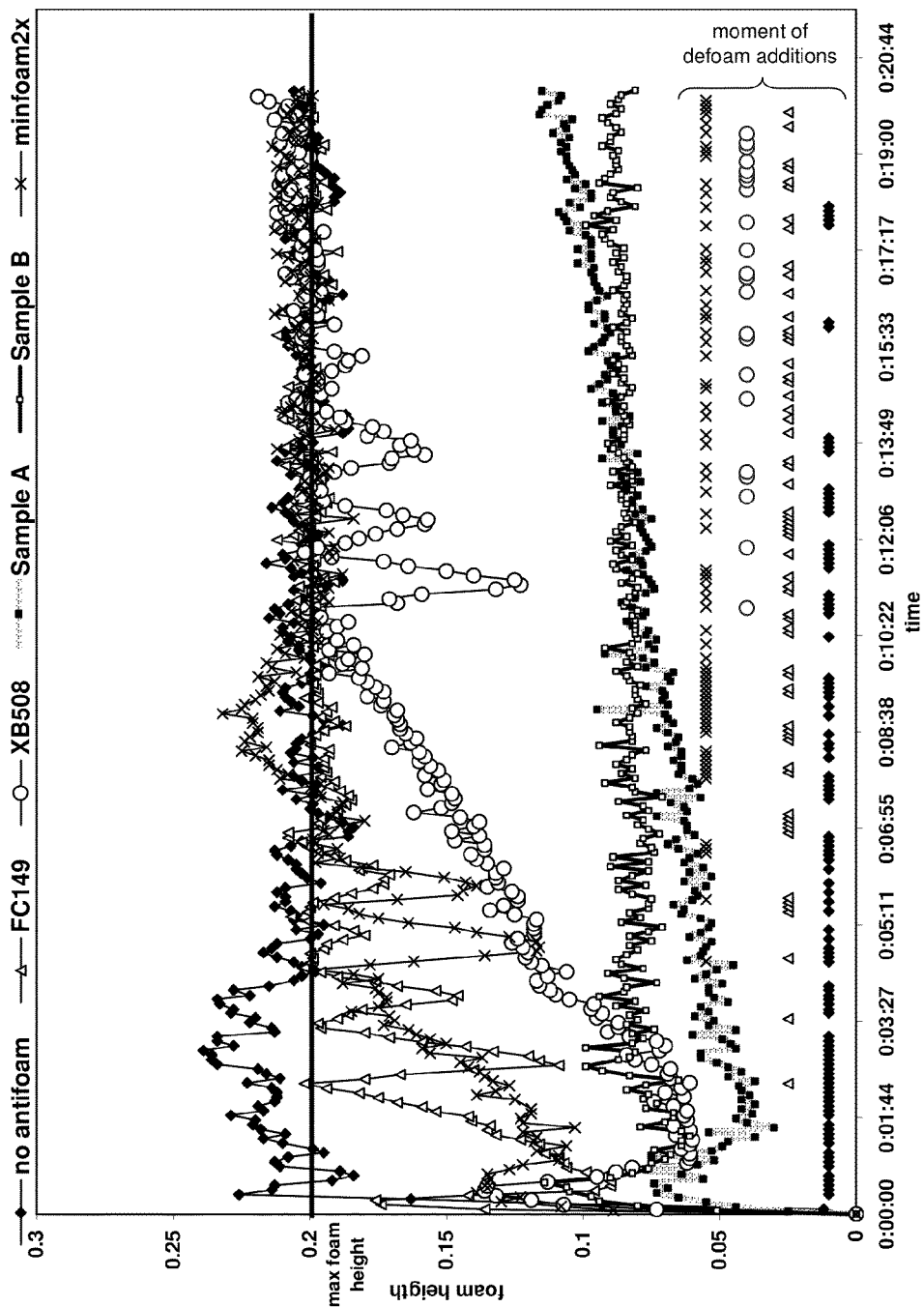
FIG. 2 is a plot of foam height as a function of time and number of additions for foam control agents according to the invention compared with commercial products.

FIG. 2 provides the results for a repeat of the above example, again showing the superiority of the foam control agents of the current invention in foam control in this application. The results of this experiment are also summarized in Table 2.

TABLE 2

| Product | Adds of defoam |
| --- | --- |
| NO ANTIFOAM (comparative example) | 139 |
| FC149 300 ul (comparative example) | 63 |
| XB508 300 ul (comparative example) | 22 |
| Invention Sample A 300 ul (invention example) | 0 |
| Invention Sample B 300 ul (invention example) | 0 |
| Minfoam 2x 300 ul (comparative example) | 79 |

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A foam control agent of formula I:

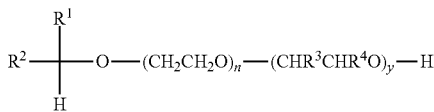

wherein $R^1$ and $R^2$ are each independently hydrogen or a linear or branched alkyl group containing from 1 to about 18 carbon atoms, provided that $R^1$ and $R^2$ together contain from about 8 to about 18 carbon atoms, and further provided that less than about 10 mole percent of $R^1$ or $R^2$ is hydrogen; $R^3$ and $R^4$ are each independently hydrogen or an alkyl radical containing 2 carbon atoms; n is an average value ranging from about 3 to about 40; and y is an average value ranging from 0.5 to 3.5, and wherein $R^3$ and $R^4$ together contain 2 carbon atoms.

2. A foam control agent according to claim 1 wherein $R^1$ and $R^2$ are each independently hydrogen or a linear or branched alkyl group containing from 1 to about 15 carbon atoms and $R^1$ and $R^2$ together contain from about 8 to about 16 carbon atoms.

3. A foam control agent according to claim 1 wherein $R^1$ and $R^2$ are each independently hydrogen or a linear or branched alkyl group containing from 1 to about 14 carbon atoms and $R^1$ and $R^2$ together contain from about 9 to about 14 carbon atoms.

4. A foam control agent according to claim 1 having the formula II:

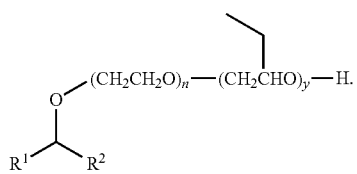

5. A foam control agent according to claim 4 wherein n is an average value ranging from about 3 to about 15.

6. A foam control agent according to claim 4 wherein y is an average value ranging about 1 to about 2.5.

7. A foam control agent according to claim 4 wherein $R^1$ and $R^2$ are each independently a linear or branched alkyl containing 2-12 carbon atoms and together contain from about 11 to about 13 carbon atoms.

8. A foam control agent according to claim 4 wherein $R^1$ and $R^2$ together with the carbon to which they are attached form linear dodecane.

9. A foam control agent according to claim 4 having the formula:

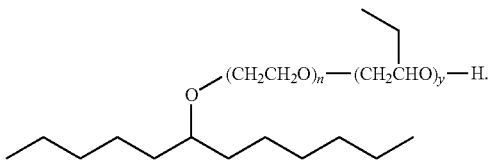

10. A foam control agent according to claim 4 wherein n is 9.

11. A foam control agent according to claim 4 wherein n is 12.

12. A method for controlling foam in a fermentation process, the method comprising using in the fermentation process a foam control agent according to claim 1.

13. A method according to claims 12 wherein the fermentation process is biofuel production.

14. A method according to claim 12 wherein the fermentation process is ethanol production.

15. A method according to claim 12 wherein the fermentation process is sugar cane based bioethanol production.

* * * * *